(12) United States Patent
Hartley et al.

(10) Patent No.: US 7,914,572 B2
(45) Date of Patent: Mar. 29, 2011

(54) SIDE BRANCH STENT GRAFT CONSTRUCTION

(75) Inventors: David Ernest Hartley, Subiaco (AU); Susan Morriss, Fremantle (AU); Werner D. Ducke, Greenwood (AU); Timothy A. Chuter, Atherton, CA (US)

(73) Assignees: William A. Cook Australia Pty. Ltd., Queensland (AU); Cook Incorporated, Bloomington, IN (US)

( * ) Notice: Subject to any disclaimer, the term of this patent is extended or adjusted under 35 U.S.C. 154(b) by 1058 days.

(21) Appl. No.: 11/706,114

(22) Filed: Feb. 13, 2007

(65) Prior Publication Data
US 2007/0219621 A1  Sep. 20, 2007

Related U.S. Application Data

(60) Provisional application No. 60/776,423, filed on Feb. 23, 2006, provisional application No. 60/773,240, filed on Feb. 13, 2006.

(51) Int. Cl.
*A61F 2/06* (2006.01)
(52) U.S. Cl. ..................... 623/1.35; 623/1.16
(58) Field of Classification Search .................. 623/1.35
See application file for complete search history.

(56) References Cited

U.S. PATENT DOCUMENTS

| | | | | |
|---|---|---|---|---|
| 5,609,627 A * | 3/1997 | Goicoechea et al. | ......... | 128/898 |
| 5,676,696 A * | 10/1997 | Marcade | ..................... | 623/1.35 |
| 5,676,697 A * | 10/1997 | McDonald | ..................... | 623/1.35 |
| 5,984,955 A * | 11/1999 | Wisselink | ..................... | 623/1.35 |
| 6,019,788 A * | 2/2000 | Butters et al. | ................ | 623/1.35 |
| 6,210,429 B1 * | 4/2001 | Vardi et al. | ................... | 623/1.11 |
| 6,645,242 B1 | 11/2003 | Quinn | | |
| 7,771,462 B1 * | 8/2010 | Davidson et al. | ............ | 623/1.11 |
| 2002/0111665 A1 * | 8/2002 | Lauterjung | ..................... | 623/1.1 |
| 2002/0156521 A1 * | 10/2002 | Ryan et al. | ................... | 623/1.13 |
| 2002/0193864 A1 * | 12/2002 | Khosravi et al. | ............. | 623/1.13 |
| 2004/0230287 A1 | 11/2004 | Hartley et al. | | |
| 2006/0155359 A1 * | 7/2006 | Watson | ........................ | 623/1.13 |

FOREIGN PATENT DOCUMENTS

| | | |
|---|---|---|
| WO | WO 03/082153 | 10/2003 |
| WO | WO 2005/034808 | 4/2005 |
| WO | WO 2005/034809 | 4/2005 |
| WO | WO 2005/096996 | 10/2005 |
| WO | WO 2006/113501 | 10/2006 |

* cited by examiner

*Primary Examiner* — Paul Prebilic
(74) *Attorney, Agent, or Firm* — Richard J. Godlewski

(57) ABSTRACT

A stent graft (10) has a tubular body (12) of a biocompatible material and at least one fenestration (18, 20). The or each fenestration has a tubular side branch stitched into it with a portion of the tubular side branch extending within the tubular body and a portion of the tubular side branch extending exteriorly of the tubular body. The stitching by which the tubular side branch is mounted into the fenestration extends circumferentially and diagonally from one end of the tubular side branch to the other such that the tubular side branch extends from the tubular body at an angle thereto. The tubular side branch has a resilient ring around at least one and preferably both ends thereof and a self expanding stent in between them. The tubular side branch can have a circumferential linear portion (46) at an inner end to engage against the inner wall (58) of the tubular body. The tubular side branch can have a stent made from a single wire forming a first ring (45), a second ring (47), the second ring defining a plane which is substantially parallel to and spaced axially apart from the plane of the first ring and a number of helical wire portions (49) extending between the first and second ring. Preferably the wire is a shape memory wire such as Nitinol™ wire.

10 Claims, 6 Drawing Sheets

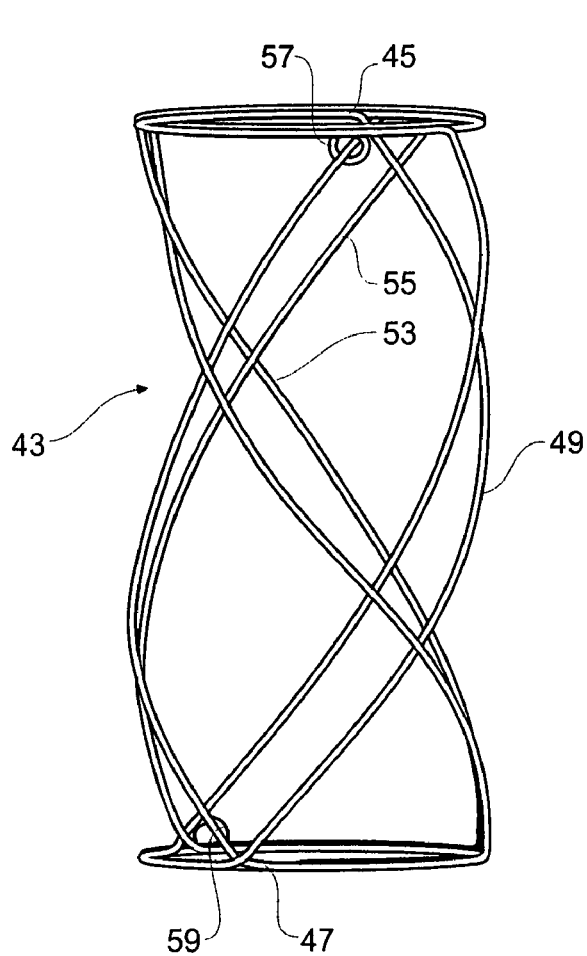
*Fig 10A*
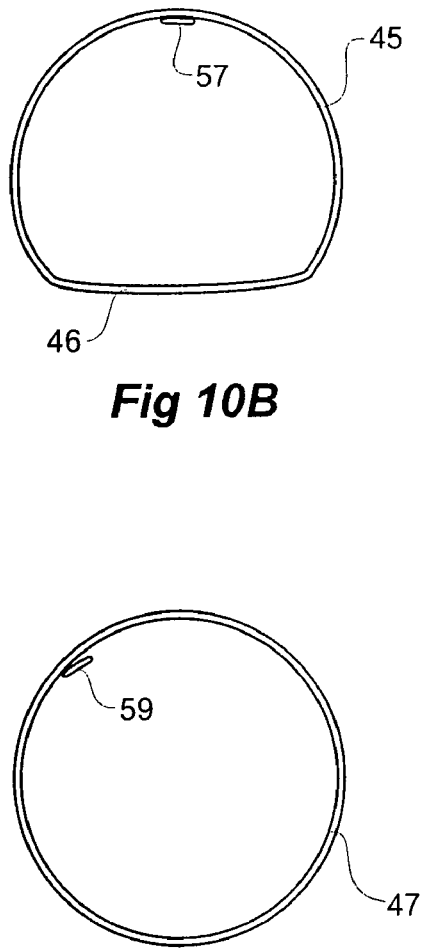
*Fig 10B*
*Fig 10C*
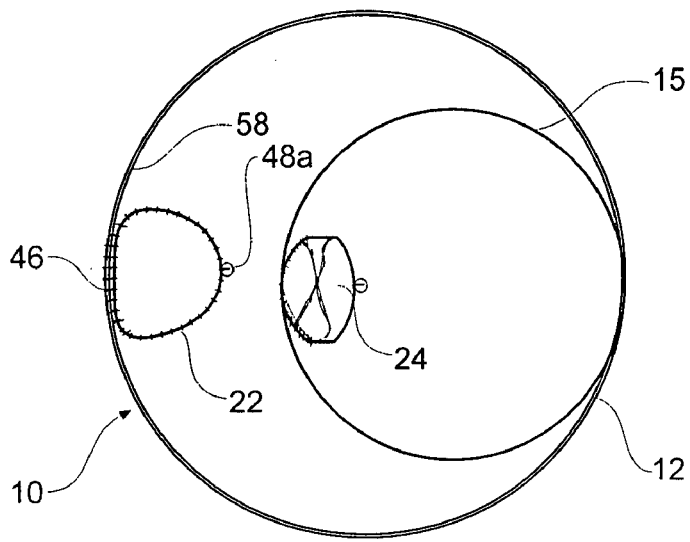
*Fig 11*

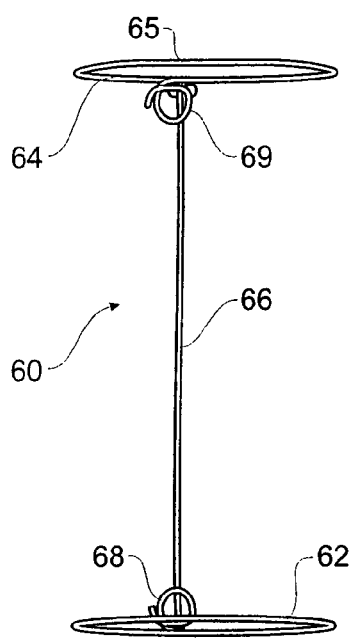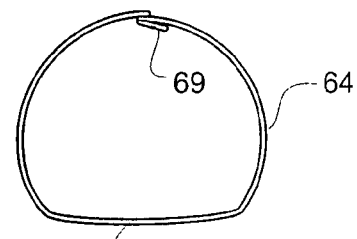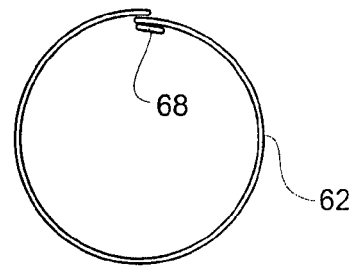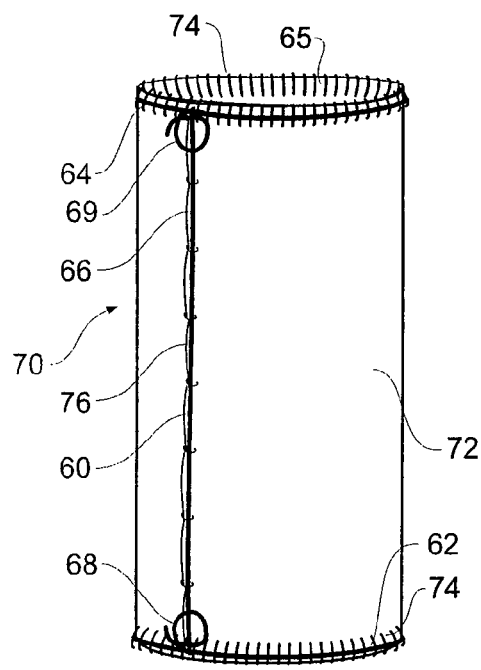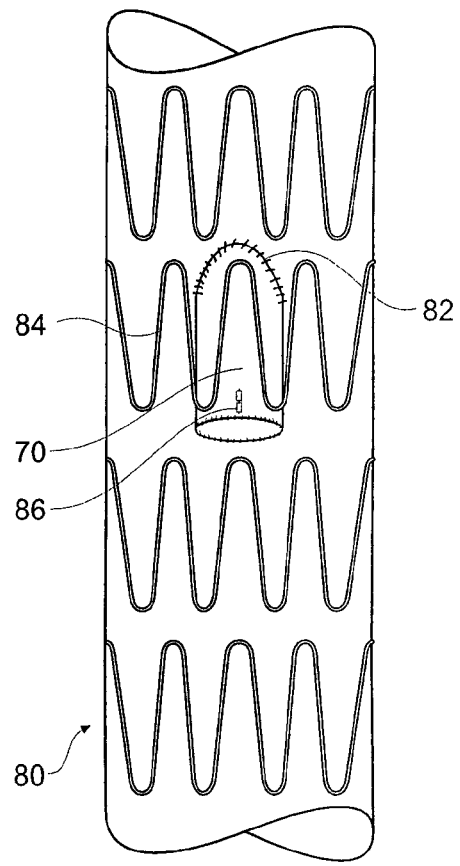
Fig 12A
Fig 12B
Fig 12C
Fig 13
Fig 14

SIDE BRANCH STENT GRAFT CONSTRUCTION

CROSS-REFERENCE TO RELATED APPLICATIONS

This application claims priority of provisional application Ser. No. 60/776,423, filed Feb. 23, 2006 and provisional application Ser. No. 60/773,240 filed Feb. 13, 2006.

TECHNICAL FIELD

This invention relates to a medical device and more particularly to a stent graft for endovascular deployment

BACKGROUND OF THE INVENTION

Stent grafts have been devised for endovascular deployment to bypass a diseased portion of a vessel and such stent grafts can be deployed into body vessels such as the aorta. Where there are branches from the body vessel such as the coeliac artery, the superior mesenteric artery and the renal arteries it is desirable to have a fenestration in the stent graft so that an extension arm can be placed through the fenestration to allow flow into the branch vessel.

In the renal and suprarenal region of aorta, the use of stent graft with fenestrations in the wall of the stent graft provides difficulty for catheterisation and sealing and there have been proposed stent grafts with internal branches into which can be deployed a side arm extension to extend from the internal branch of the stent graft into a branch vessel and so that the side arm extension can seal with in the internal branch.

In some regions of the aorta such as the thoracic arch and the infra renal region there is often insufficient length of stent graft proximally of the fenestration to allow an internal arm of sufficient length to be used. If the internal arm is made too short then there is insufficient length for sealing of the extension arm.

It is the object of this invention to provide a solution to this problem or at least to provide the practitioner with an alternative stent graft construction.

The invention will be particularly discussed in relation to deployment of a stent graft into the renal and suprarenal regions of the aorta for deployment of a stent graft into coeliac artery, the superior mesenteric artery and the renal arteries, however, the invention is not so limited and may be applied to other regions where there are branches from a main graft such as in the thoracic arch.

Throughout this specification the term distal, when used with respect to a portion of the aorta, a deployment device or a prosthesis, means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form, therefore, the invention is said to reside in a stent graft comprising a tubular body of a biocompatible material, at least one fenestration in the tubular body and a tubular side branch sealingly received in the at least one fenestration such a that an inner portion of the tubular side branch extends within the tubular body and an outer portion of the tubular side branch extends exteriorly of the tubular body.

It will be seen that by having the tubular side branch mounted into the fenestration and extending in both directions from the fenestration sufficient length for sealing of an extension arm into the tubular side branch is provided without having the tubular side branch extending too far into the stent graft tubular body.

In the case where the stent graft according to the present invention is intended for use in the suprarenal region, the internal portion of the tubular side branch extends toward the proximal end of the stent graft from the fenestration.

In a preferred embodiment the tubular body has a tapered portion and the fenestration is in the tapered portion. In the region of the coeliac and superior mesenteric arteries, the aorta tapers as these major branch vessels extend from the aorta and tapering of the stent graft assists with maintaining a good blood flow and pressure in the stent graft.

Preferably the tubular side branch is mounted into the fenestration by being stitched to the tubular body around the periphery of the fenestration.

Preferably the stitching by which the tubular side branch is mounted and sealed into the fenestration extends circumferentially and diagonally from one end of the tubular side branch to the other such that the tubular side branch extends from the tubular body at an angle thereto. The fenestration may be in the tapered portion of the tubular body and wherein the stitching by which the tubular side branch is mounted into the fenestration extends circumferentially and diagonally from one end of the tubular side branch to the other the angle between the tubular side branch and the wall of the tubular body in that region may be such that the tubular side branch extends substantially parallel to the tubular body as a whole.

In a preferred embodiment the tubular side branch comprises a resilient ring around at least one and preferably both ends thereof. The resilient ring is flexible so that it can be collapsed along with a stent graft when it is compressed and retailed in a deployment device but when released opens to a substantially circular form and provides a relatively rigid structure against which a self expanding or balloon expandable stent can be expanded when placing a extension arm into the tubular side branch. The resilient ring or rings my have a diameter which is 10% to 15% less than that of the tubular side branch. For instance when the tubular side branch has a diameter of 8 mm the resilient ring may have a diameter of 7 mm.

The or each ring may be formed from at least two turns and preferably three turns of a shape memory wire such as Nitinol™ wire and the ends of the Nitinol™ wire may terminate in loops. The use of the loops prevent sharp ends from the Nitinol™ wire from digging into the vasculature into which the stent graft is deployed. The rings are stitched to the tube by stitching. The rings can alternatively be formed from stainless steel wire, plastics material or other suitable material. Stitching of the loops on the rings to the biocompatible graft material also prevents the resilient rings from being expanded by the pressure of a self expanding or balloon expandable stent placed therein and expanded.

Between the rings on the tubular side branch there may be a stent formed from a resilient material. The resilient stent may be formed from Nitinol™ wire or stainless steel. The stent can comprise at least one helical strut, a longitudinal strut or a zig-zag stent.

In one embodiment the resilient stent defines a cylindrical form having a diameter less than that of the tubular side branch to define a self contracting stent and hence when sewn onto the outside of the tube using stitching it provides a diameter reducing effect on the tubular side branch.

Also provided on the tubular side branch may be radiopaque markers adjacent each of the ends of the tubular side branch. These markers enable the physician to visualise the tubular side branch during an operation to assist with correct placement of a leg extension into the tubular side branch.

In a preferred embodiment the tubular side branch may extend beyond the fenestration externally of the tubular body. Such an extension may have one or more stents thereon to maintain patency.

In an alternative form, the invention is said to reside in a stent graft comprising a tubular body of a biocompatible material, at least one fenestration in the tubular body and a tubular side branch sealingly received in the fenestration such that a portion of the tubular side branch extends within the tubular body and a portion of the tubular side branch extends exteriorly of the tubular body, the portion of the tubular side branch extending within the tubular body comprising a circumferential end having a substantially linear portion and the linear portion being engaged against an inner wall of the tubular body.

It will be seen that by having the tubular side branch mounted into the fenestration and extending in both directions from the fenestration sufficient length for sealing of an extension arm into the tubular side branch is provided without having the tubular side branch extending too far into the stent graft tubular body. The linear portion of the inner circumferential end engaging against the wall provides a low profile for the inner end within the tubular body. This also assists with enabling a physician to extend a guide wire into the side arm because a guide wire being directed down along the inner wall of the tubular body will more easily enter the side branch where the circumference extends around and along the wall for some distance.

In a preferred embodiment the resilient rings and the stent formed between the rings may be a single portion of material. Such a combined stent and rings may comprise a portion of wire forming a first ring, a second ring, the second ring defining a plane which is substantially parallel to and spaced axially apart from the plane of the first ring and a plurality of helical wire portions extending between the first and second ring. Preferably the wire is a shape memory wire such as Nitinol™ wire.

Preferably the helical portions extend in both clockwise and anticlockwise directions between the rings at each end.

Preferably each ring is be formed from but not limited to two turns of a shape memory wire such as Nitinol™ wire and the ends of the Nitinol™ wire may terminate in loops. Part of each ring at each end can be formed by circumferential portions extending from each helical portion.

In an alternative form the invention comprises a stent graft comprising a tubular body of a biocompatible material, at least one fenestration in the tubular body and a tubular side branch sealingly received in the fenestration such a that an inner portion of the tubular side branch extends within the tubular body and an outer portion of the tubular side branch extends exteriorly of the tubular body, the tubular side branch comprises a reinforcement stent and wherein the reinforcement stent comprises a portion of wire forming a first ring, a second ring, the second ring defining a plane which is substantially parallel to and spaced axially apart from the plane of the first ring and a plurality of helical wire portions extending between the first and second ring and wherein the inner portion comprises a circumferential end having a substantially linear portion and the linear portion being engaged against an inner wall of the tubular body.

BRIEF DESCRIPTION OF THE DRAWING

This then generally describes the invention but to assist with understanding reference will now be made to the accompanying drawings which show preferred embodiments of the invention.

In the drawings:

FIGS. 10A, 10B and 10C show views of the combined ring and helical portion stent used on the side arm according to one embodiment of the present invention;

FIG. 11 shows a view into the stent graft shown in FIG. 7 in the direction shown by the arrow 7 in FIG. 7;

FIGS. 12A, 12B and 12C show views of combined rings and longitudinal strut stent used on the side arm according to one embodiment of the present invention;

FIG. 13 shows a detailed view of a tubular side branch using the stent shown in FIG. 12; and FIG. 14 shows a portion of a stent graft utilising the tubular side branch shown in FIG. 13.

DETAILED DESCRIPTION

Figures 1, 2:
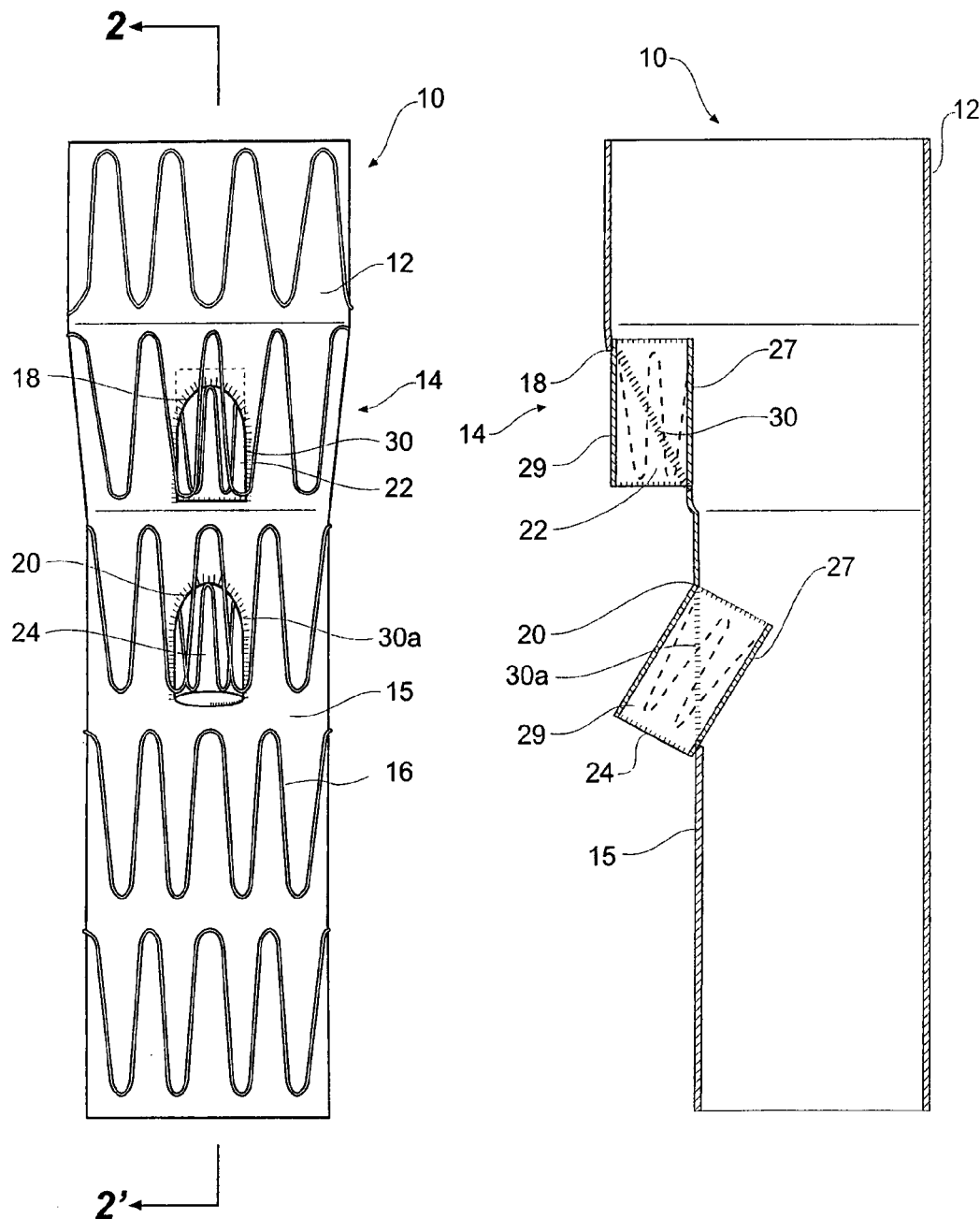
FIG. 1 shows a first embodiment of stent graft according to the present invention.
FIG. 2 shows a cross-sectional view of the stent graft of FIG. 1 along the fines 2-2' of FIG. 1.

Looking more closely at the drawings and in particular FIGS. 1 to 2 showing a first embodiment of a stent graft according to the present invention, it will be seen that stent graft 10 has a tubular body 12 which includes a tapered central region 14 and a lower parallel sided portion 15. The tubular body is supported by stents 16. Preferably these stents are self expanding Gianturco zig zag Z stents but other forms of stents may also be included.

In the tapered region 14, there is a fenestration 18 and in the lower parallel sided portion 15 of the tubular body 12 there is another fenestration 20. Mounted into each of the fenestrations 18 and 20 are tubular side branches 22 and 24 respectively.

As can be particularly seen in FIG. 2, the tubular side branches 22 and 24 each have an inner portion 27 which extends within the tubular body of the stent graft and an outer portion 29 which extends outside of the tubular body of the stent graft. The tubular side branches are depicted as being longitudinally aligned with each other but their circumferential and longitudinal position may vary depending upon the configuration of side arteries in the vessel into which the stent graft is to be deployed. It will be noted that in this embodiment both the tubular side branch 22 and the tubular side branch 24 have their external portions facing distally.

Each of the tubular side branches 22 and 24 are stitched into the periphery of the fenestration by stitching 30 and 30a respectively. The stitching extends circumferentially and diagonally from one end of the tubular side branch to the other. Where the tubular side branch 22 is mounted into the tapered portion 14 of the tubular body 12, the angled stitching 30 in fact means that the tubular side branch 22 extends substantially parallel to the tubular body 12.

On the other hand the tubular side branch 24 mounted into the fenestration 20 with diagonal stitching 30a is in a substantially straight sided portion of the tubular body 12 and therefore the tubular side branch extends out at a angle to the tubular body 20.

Figure 3:
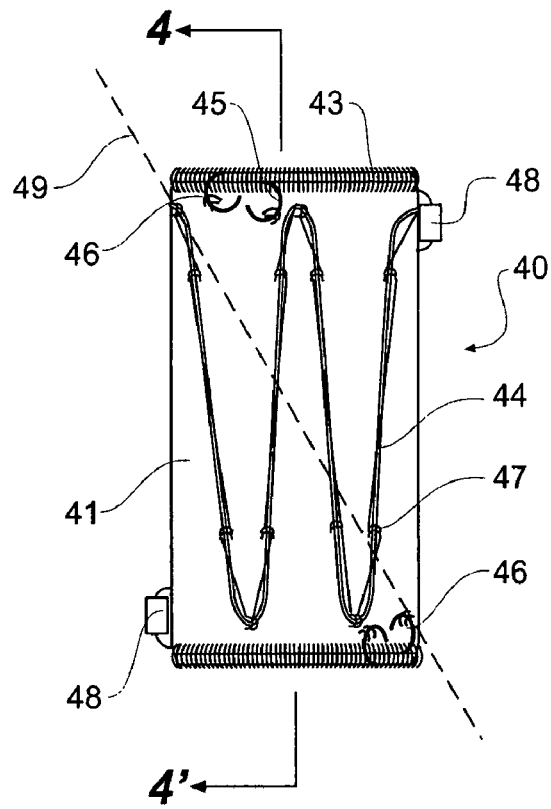
FIG. 3 shows a detailed view of a tubular side branch suitable for use with the present invention.
Figure 4:
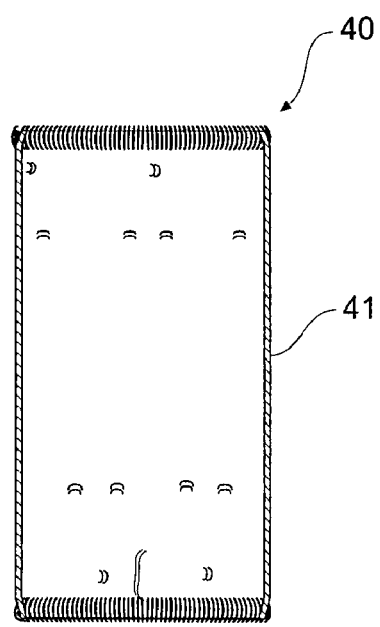
FIG. 4 shows a cross-sectional view of the tubular side branch of FIG. 3.

Detailed construction of one embodiment of each of the tubular side branches is shown in FIGS. 3 and 4. FIG. 3 shows a side view of a tubular side branch according to one embodiment of the invention before it is stitched into the fenestration in a main stent graft. FIG. 4 shows a cross-section of embodiment shown in FIG. 3 along the line 4-4' in FIG. 3.

The tubular side branch 40 comprises a tubular body 41 of a biocompatible graft material. At each end of the tubular body 41, a resilient ring 43 is stitched onto the biocompatible material. The resilient ring is preferably formed of two and preferably three turns of Nitinol™ wire, the ends of which terminate in loops 45 which are stitched by stitching 46 to the biocompatible graft material body 41.

Between the resilient rings 43 on the tubular side branch 40 there is a stent 44 formed from a resilient material. The resilient stent may be formed from Nitinol™ wire or stainless steel. The stent 44 is stitched onto the tubular body 41 with stitching 47.

Radiopaque markers 48 are provided at each end of the tubular side branch so that a physician can visualise the position of the tubular side branch when operating within a patient.

The dotted line 49 shows the approximate line of stitching by which the tubular side branch 40 is mounted into the fenestrations as discussed in relation to FIGS. 1 and 2. It will be noted that the line of stitching extends circumferentially and diagonally from one side at one end to the other side at the other end.

Figure 5:
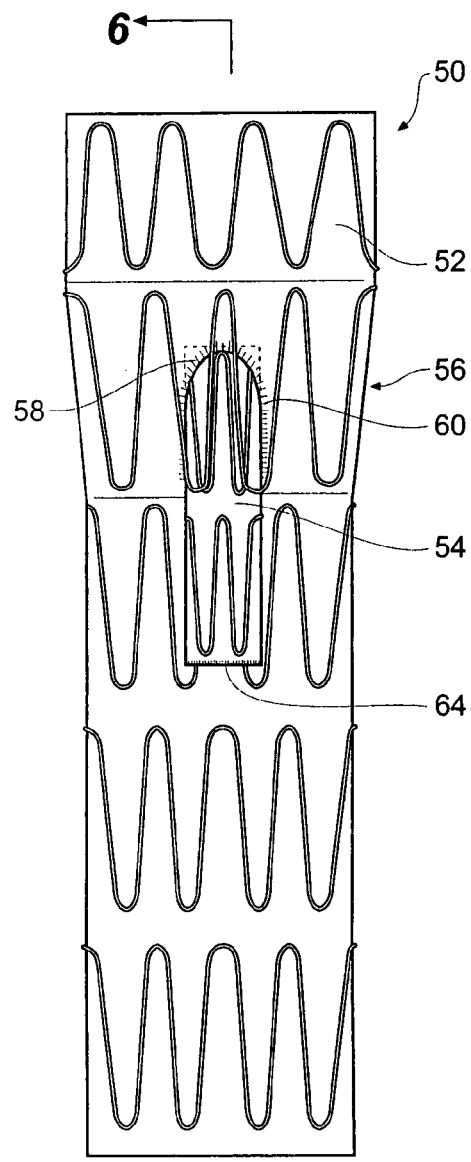
FIG. 5 shows a further embodiment of the stent graft according to the present invention.
Figure 6:
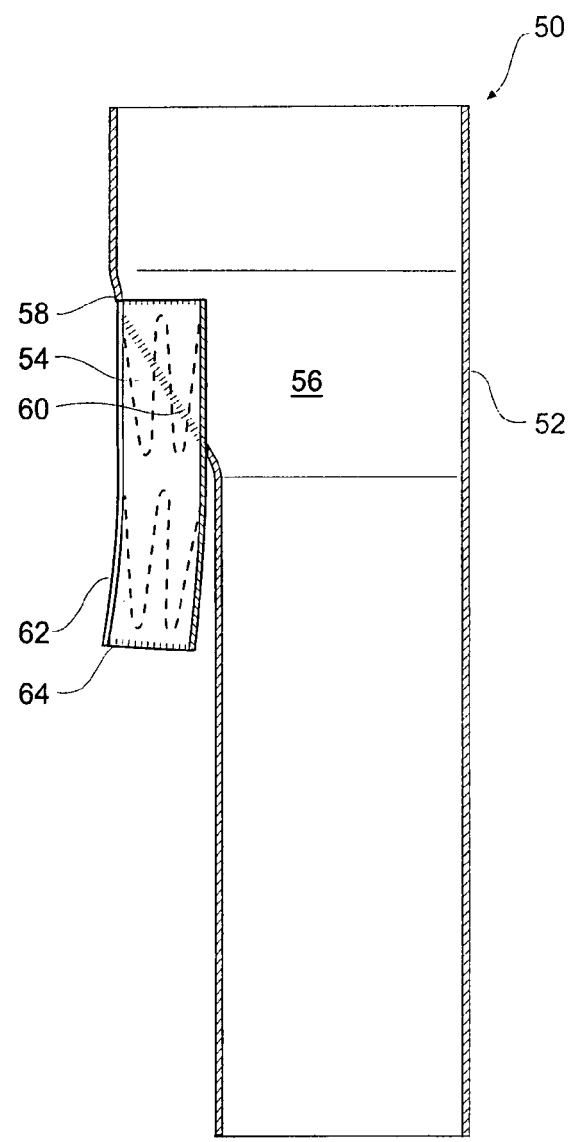
FIG. 6 shows a cross-sectional view of the stent graft of FIG. 5 along the lines 6-6' of FIG. 5.

FIGS. 5 and 6 show an alternative embodiment of a stent graft incorporating a tubular side branch according to the present invention.

In this embodiment, the stent graft 50 has a tubular body 52 of a graft material and a tubular side branch 54 stitched into a tapered portion 56 of the tubular body 52. The tubular side branch 54 is received in a fenestration 58 by stitching 60. In this embodiment the tubular side branch 54 extends exteriorly of the stent graft with a tubular extension 62 terminating in a resilient ring 64. It will be noted that in this embodiment the tubular side branch 54 has its external portion facing distally.

Figure 7:
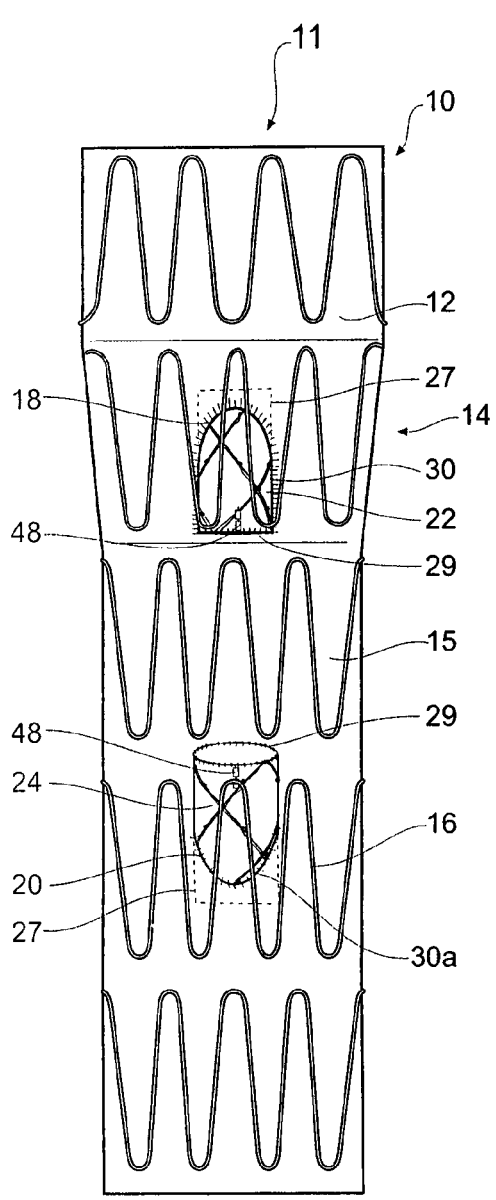
FIG. 7 shows an alternative embodiment of stent graft according to the present invention.

FIG. 7 shows an alternative embodiment of a stent graft according to the present invention. FIG. 7 uses the same reference numerals as FIG. 1 for corresponding items. The stent graft 10 has a tubular body 12 which includes a tapered central region 14 and a lower parallel sided portion 15. The tubular body is supported by stents 16. Preferably these stents are self expanding Gianturco zig zag Z stents but other forms of stents may also be included.

In the tapered region 14, there is a fenestration 18 and in the lower parallel sided portion 15 of the tubular body 12 there is another fenestration 20. Mounted into each of the fenestrations 18 and 20 are tubular side branches 22 and 24 respectively.

The tubular side branches 22 and 24 each have an inner portion 27 which extends within the tubular body of the stent graft and an outer portion 29 which extends outside of the tubular body of the stent graft.

Each of the tubular side branches 22 and 24 are stitched into the periphery of the fenestration by stitching 30 and 30a respectively. The stitching extends circumferentially and diagonally from one end of the tubular side branch to the other. Where the tubular side branch 22 is mounted into the tapered portion 14 of the tubular body 12, the angled stitching 30 in fact means that the tubular side branch 22 extends substantially parallel to the tubular body 12.

The tubular side branch 24 mounted into the fenestration 20 with diagonal stitching 30a is in a substantially straight sided portion of the tubular body 12 and therefore the tubular side branch extends out at an angle to the tubular body 20.

It will be noted that in this embodiment the tubular side branch 22 has its external portion facing distally and the tubular side branch 24 has its external portion facing proximally.

Figure 8:
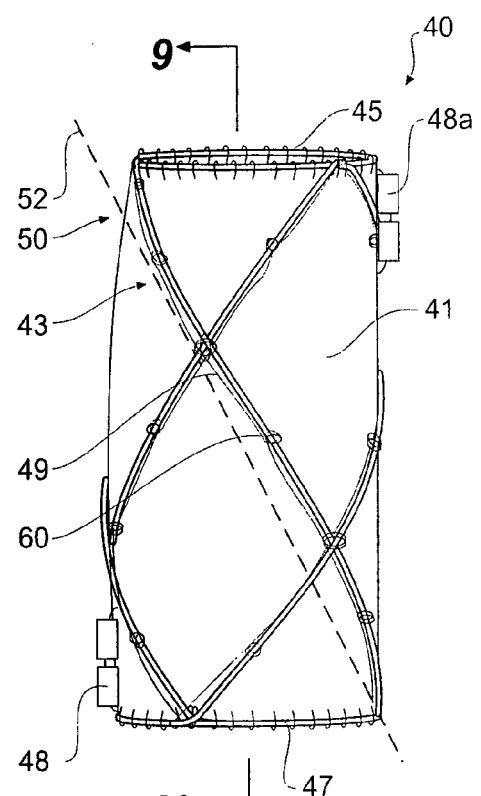
FIG. 8 shows a detailed view of a tubular side branch suitable for use with the embodiment of stent graft shown in FIG. 7 according to present invention.
Figure 9:
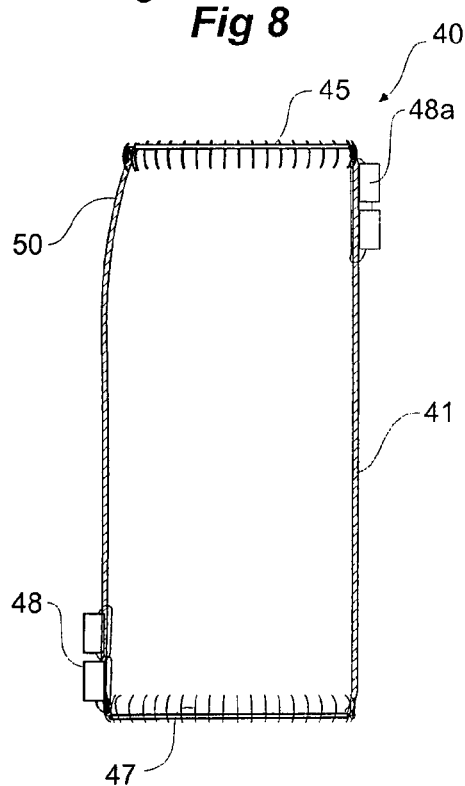
FIG. 9 shows a cross-sectional view of the tubular side branch of FIG. 8 along the lines 9-9' of FIG. 8.

Detailed construction of each of the tubular side branches shown in FIG. 7 is shown in FIGS. 8 and 9.

FIG. 8 shows a side view of a tubular side branch according to one embodiment of the invention before it is stitched into the fenestration in a main stent graft. FIG. 9 shows a cross-section of embodiment shown in FIG. 8 along the line 9-9' in FIG. 8.

The tubular side branch 40 comprises a tubular body 41 of a biocompatible graft material. Surrounding and supporting the tubular body 41 is a stent 43. The stent 43 comprises an integral assembly of a first ring 45, a second ring 47, the second ring 47 defining a plane which is substantially parallel to and spaced axially apart from the plane of the first ring 45, and helical wires 49 extending between the first and second rings. The stent 43 is shown in more detail in FIG. 10A. The stent may be formed from Nitinol™ wire or stainless steel. The stent 43 is stitched onto the tubular body 41 with stitching 60.

The tubular body is shaped at one end by the ring 45 having a linear portion on one side, as shown in more detail in FIG. 10B, such that the tubular body curves in at 50.

Radiopaque marker 48 is provided at the outer end of the tubular side branch so that a physician can visualise the position of the tubular side branch on the stent graft when operating within a patient. Radiopaque markers 48a can also be provided at the inner end of the tubular side branch so that a physician can visualise the position of the tubular side branch within the stent graft when catheterising it when operating within a patient.

The dotted line 52 shows the approximate line of stitching by which the tubular side branch 40 is mounted into the fenestrations as discussed in relation to FIGS. 1 and 2. It will be noted that the line of stitching extends circumferentially and diagonally from one side at one end to the other side at the other end.

FIGS. 10A, 10B and 10C show one embodiment of construction for the stent 43 as shown in FIG. 8. The stent comprises Nitinol wire of a diameter of 0.006 in. formed into a first ring 45 of least two turns of wire, A second ring 47 formed from at least two turns of wire and helical arms 49 between them. In this embodiment there are three helical wires 53 extending in a clockwise direction and three wires 55 extending in an anticlockwise direction to, in effect, form a loose braid. In fact the entire stent is formed from a single length of wire starting at loop 57 and terminating at loop 59. The upper ring 45 has a circumferential shape as shown in FIG. 10B. The circumference of the ring 45 includes a linear portion 46. This linear portion 46, when the stent is installed on a side arm and the side arm is fitted into a stent graft, engages against the wall of the stent graft as shown in FIG. 6.

FIG. 10C shows the shape of the rings 47 at the end of the tubular side branch which in use is intended to be outside the stent graft in use.

FIG. 11 shows a view into the stent graft shown in FIG. 7 in the direction shown by the arrow 11 in FIG. 7. The side arm 22 has its linear portion 46 engaged against the inner wall 58 of the tubular body 12. The side arm 24 is mounted into the lower parallel sided portion 15.

FIGS. 12A, 12B and 12C show views of combined rings and longitudinal strut forming a stent 60 used on the side arm according to an alternative embodiment of the present invention. In this embodiment the stent 60 comprises upper and lower rings 62 and 64 joined by a single longitudinal strut 66. The stent is formed from a single piece of Nitinol or similar wire and the wire terminates in respective loops 68 and 69. FIG. 12B shows the ring 64 with loop 69 and a flattened portion 65 which fits against the inner wall of the stent graft as discussed earlier. FIG. 12C shows the ring 62 with the loop 68.

FIG. 13 shows a detailed view of a tubular side branch using the stent shown in FIG. 12. The tubular side branch 70 comprises a tubular portion of biocompatible graft material 72 with the stent 60 outside of it so that the ring 62 is at one end of the tubular body and the ring 64 is at the other end of the tubular body and the strut 66 extends along the outside of the tubular body. The rings 62 and 64 are stitched to the tubular body by stitching 74 and the strut 66 is stitched to the tubular body by stitching 76.

FIG. 14 shows a portion of a stent graft utilising the tubular side branch shown in FIG. 13. The stent graft 80 has a fenestration 82 into which the tubular side branch 70 is sewn. One of the stents 84 of the stent graft 80 passes over the tubular side branch 70. Radiopaque markers 86 are provided on the terminal end of the tubular side branch 70.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising a tubular body of a biocompatible material, a fenestration in the tubular body and a tubular side branch sealingly received in the fenestration, the tubular side branch being mounted into the fenestration whereby an inner portion of the tubular side branch extends within the tubular body and an outer portion of the tubular side branch extends exteriorly of the tubular body, the tubular side branch comprising a resilient ring around both ends thereof and the tubular side branch being mounted into the fenestration by being fastened by a fastening arrangement to the tubular body around the periphery of the fenestration and the fastening arrangement extending circumferentially and diagonally from one end of the tubular side branch to the other end of the tubular side branch such that the tubular side branch extends from the tubular body at an angle thereto.

2. A stent graft as in claim 1, the stent graft comprising a proximal end and a distal end and wherein the inner portion of the tubular side branch extends toward the proximal end of the stent graft from the fenestration.

3. A stent graft as in claim 1 wherein the tubular body comprises a tapered portion and the fenestration is in the tapered portion.

4. A stent graft as in claim 1 wherein the fastening arrangement comprises stitching.

5. A stent graft as in claim 1 wherein each ring is formed from one to three turns of a shape memory wire and the ends of the wire terminate in loops and each ring is formed from stainless steel wire.

6. A stent graft as in claim 1 further comprising a stent formed from a resilient material on the tubular side branch.

7. A stent graft as in claim 6 wherein the stent comprises a longitudinal strut.

8. A stent graft as in claim 1 wherein the tubular side branch comprises radiopaque markers on the outer portion of the tubular side branch.

9. A stent graft as in claim 1 wherein the tubular side branch extends beyond the fenestration externally of the tubular body.

10. A stent graft as in claim 5 wherein the tubular side branch comprises an inner end and an outer end and the ring at the inner end of the tubular side branch comprises a linear portion and the linear portion is engaged against an inner wall of the tubular body.

* * * * *